(12) United States Patent
Miller et al.

(10) Patent No.: US 8,557,995 B2
(45) Date of Patent: *Oct. 15, 2013

(54) SOLID DISPERSIONS CONTAINING KINASE INHIBITORS

(75) Inventors: Jonathan M. Miller, Lindenhurst, IL (US); Rajeev Gokhale, Helios (SG); Eric A. Schmitt, Libertyville, IL (US); Yi Gao, Vernon Hills, IL (US); Justin Lafountaine, Chicago, IL (US); Lloyd Dias, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 24 days.

This patent is subject to a terminal disclaimer.

(21) Appl. No.: 13/154,562

(22) Filed: Jun. 7, 2011

(65) Prior Publication Data

US 2011/0306632 A1  Dec. 15, 2011

Related U.S. Application Data

(60) Provisional application No. 61/352,862, filed on Jun. 9, 2010.

(51) Int. Cl.
*A61K 31/44* (2006.01)
*C07D 513/02* (2006.01)

(52) U.S. Cl.
USPC .......................................... 546/114; 514/338

(58) Field of Classification Search
USPC .......................................... 514/338; 546/114
See application file for complete search history.

(56) References Cited

U.S. PATENT DOCUMENTS

| | | | |
|---|---|---|---|
| 6,763,607 | B2 | 7/2004 | Beyerinck et al. |
| 2002/0009494 | A1 | 1/2002 | Curatolo et al. |
| 2003/0185893 | A1 | 10/2003 | Beyerinck et al. |
| 2003/0219489 | A1 | 11/2003 | Curatolo et al. |
| 2004/0194338 | A1 | 10/2004 | Beyerinck et al. |
| 2005/0031692 | A1 | 2/2005 | Beyerinck et al. |
| 2007/0155776 | A1 | 7/2007 | Betschmann et al. |
| 2008/0317851 | A1 | 12/2008 | Appel et al. |
| 2010/0144783 | A1* | 6/2010 | Michaelides ............... 514/301 |
| 2010/0310648 | A1 | 12/2010 | Packhaeuser et al. |
| 2010/0311751 | A1 | 12/2010 | Schmitt et al. |

FOREIGN PATENT DOCUMENTS

| | | |
|---|---|---|
| EP | 1796642 | 5/2008 |
| WO | WO2008012617 A1 | 1/2008 |
| WO | WO2009050291 A2 | 4/2009 |
| WO | 2010/041051 | 4/2010 |
| WO | WO2010065825 A2 | 6/2010 |

OTHER PUBLICATIONS

Fiedler, "Encyclopedia of Excipients for Pharmaceuticals, Cosmetics and Related Areas," 5th Edition, Hoepfner E.M., et al., eds., Editio Cantor Verlag Aulendorf, 2002, Table of Contents.
Sharma D.K., et al., "Solubility Enhancement Strategies for Poorly Water-Soluble Drugs in Solid Dispersions: A Review," Asian Journal of Pharmaceutics, 2007, vol. 1 (1), pp. 9-19.
Sperling L. H., "Introduction to Physical Polymer Science," 2nd Edition, John Wiley & Sons, Inc., 1992, Table of Contents.
Sutton, V.R. et al., "Bcl-2 Prevents Apoptosis Induced by Perforin and Granzyme B, but Not That Mediated by Whole Cytotoxic Lymphocytes," Journal of Immunology, 1997, vol. 158 (12), pp. 5783-5790.
Tse, C. et al., "ABT-263: A Potent and Orally Bioavailable Bcl-2 Family Inhibitor," Cancer Research, 2008, vol. 68 (9), pp. 3421-3428—Including Supplementary Data.
U.S. Department of Health and Human Services Food and Drug Administration Center for Drug Evaluation and Research, Guidance for Industry, Aug. 2000, Table of Contents.
International Search Report and Written Opinion for Application No. PCT/US2011/039430, mailed on May 16, 2012.
Castro S., et al., "Use of Solid Dispersions as a Strategy to Increase Drug Dissolution Rate," Farmacotecnia [Pharmaceutical Technology], 2008, Issue. 54, pp. 24-29.
Martin C., "Pharmaceutical Extrusion Technology", Ghebre-Sellassie I., ed., Marcel Dekker, Inc., 2003, Table of Contents.
Pomeda S.M., et al., "The Effect of Co-solvents and Polyvinylpyrrolidone K-30 Solid Dispersions on Thiabendazole Solubility," Pharmaceutical Technology, pp. 85-87, (2002) best to Applicant's Knowledge.

\* cited by examiner

*Primary Examiner* — Shirley V Gembeh
(74) *Attorney, Agent, or Firm* — Susan L. Steele

(57) ABSTRACT

A solid dispersion comprises, in essentially non-crystalline form, a kinase inhibitory compound, e.g., N-(4-{4-amino-7-[1-(2-hydroxyethyl)-1H-pyrazol-4-yl]thieno[3,2-c]pyridin-3-yl}phenyl)-N'-(3-fluorophenyl)urea, dispersed in a solid matrix that comprises (a) a pharmaceutically acceptable water-soluble polymeric carrier and (b) a pharmaceutically acceptable surfactant. A process for preparing such a solid dispersion comprises dissolving the compound, the polymeric carrier and the surfactant in a suitable solvent, and removing the solvent to provide a solid matrix comprising the polymeric carrier and the surfactant and having the compound dispersed in essentially non-crystalline form therein. The solid dispersion is suitable for oral administration to a subject in need thereof for treatment of a cancer.

16 Claims, No Drawings

SOLID DISPERSIONS CONTAINING KINASE INHIBITORS

CROSS-REFERENCE TO RELATED APPLICATIONS

This application claims priority to U.S. Provisional Application Ser. No. 61/352,862 filed Jun. 9, 2010, which is incorporated by reference in its entirety.

FIELD OF THE INVENTION

The present invention relates to solid dispersions comprising compounds that inhibit protein kinases, to pharmaceutical dosage forms comprising such dispersions, to processes for preparing such dispersions and dosage forms and to methods of use thereof for treating diseases.

BACKGROUND OF THE INVENTION

Mitosis is a process by which a complete copy of a duplicated genome is segregated by the microtuble spindle apparatus into two daughter cells. Aurora-kinases, key mitotic regulators required for genome stability, have been found to be overexpressed in human tumors. There is therefore an existing need in the therapeutic arts for compounds which inhibit Aurora-kinases, compositions comprising the inhibitors and methods of treating diseases during which Aurora-kinases are unregulated or overexpressed.

The reversible phosphorylation of proteins is one of the primary biochemical mechanisms mediating eukaryotic cell signaling. This reaction is catalyzed by protein kinases that transfer the g-phosphate group of ATP to hydroxyl groups on target proteins. 518 such enzymes exist in the human genome of which ~90 selectively catalyze the phosphorylation of tyrosine hydroxyl groups Cytosolic tyrosine kinases reside intracellularly whereas receptor tyrosine kinases (RTKs) possess both extracellular and intracellular domains and function as membrane spanning cell surface receptors. As such, RTKs mediate the cellular responses to environmental signals and facilitate a broad range of cellular processes including proliferation, migration and survival.

RTK signaling pathways are normally highly regulated, yet their over-activation has been shown to promote the growth, survival and metastasis of cancer cells. Dysregulated RTK signaling occurs through gene over-expression or mutation and has been correlated with the progression of various human cancers.

The VEGF receptor (VEGFR) family consists of three RTKs, KDR (kinase insert domain-containing receptor; VEGFR2), FLT1 (Fms-like tyrosine kinase; VEGFR1), and FLT4 (VEGFR3). These receptors mediate the biological function of the vascular endothelial growth factors (VEGF-A, -B, -C, -D, -E and placenta growth factor (PlGF)), a family of homodimeric glycoproteins that bind the VEGF receptors with varying affinities.

KDR is the major mediator of the mitogenic, angiogenic and permeability-enhancing effects of VEGF-A, hereafter referred to as VEGF. Many different cell types are able to produce VEGF, yet its biological activity is limited predominately to the vasculature by way of the endothelial cell-selective expression of KDR. Not surprisingly, the VEGF/KDR axis is a primary mediator of angiogenesis, the means by which new blood vessels are formed from preexisting vessels.

FLT1 binds VEGF, VEGF-B and placental growth factor. FLT1 is expressed on the surface of smooth muscle cells, monocytes and hematopoietic stems cells in addition to endothelial cells. Activation of FLT1 signaling results in the mobilization of marrow-derived endothelial progenitor cells that are recruited to tumors where they contribute to new blood vessel formation.

FLT4 mediates the signaling of VEGF-C and VEGF-D, which mediate formation of tumor-associated lymphatic vessels (lymphangiogenesis). Lymphatic vessels are one of the routes by which cancer cells disseminate from solid tumors during metastasis.

The PDGF receptor (PDGFR) family consists of five RTK's, PDGFR-a and -b, CSF1R, KIT, and FLT3.

CSF-1R is encoded by the cellular homolog of the retroviral oncogene v-fms and is a major regulator of macrophage development. Macrophages are frequent components of tumor stroma and have been shown to modify the extracellular matrix in a manner beneficial to tumor growth and metastasis.

KIT is expressed by hematopoietic progenitor cells, mast cells, germ cells and by pacemaker cells in the gut (interstitial cells of Cajal). It contributes to tumor progression by two general mechanisms namely autocrine stimulation by its ligand, stem cell factor (SCF), and through mutations that result in ligand-independent kinase activity.

FLT3 is normally expressed on hematopoietic stem cells where its interaction with FLT3 ligand (FL) stimulates stem cell survival, proliferation and differentiation. In addition to being over-expressed in various leukemia cells, FLT3 is frequently mutated in hematological malignancies with approximately one-third of patients with acute myeloid leukemia (AML) harboring activating mutations.

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

Compounds that inhibit protein kinases such as Aurora-kinases and the VEGFR and PDGFR families of kinases have been identified. These compounds, and methods to make them, are disclosed in U.S. Patent Publication No. 2007-0155776 A1 (hereinafter the '776 publication) and U.S. patent application Ser. No. 12/632,183 (hereinafter "the '183 application"), incorporated by reference herein in their entirety.

The very low aqueous solubility of compounds, for example, of the '183 application raises challenges for the formulator, especially where there is a need to maintain acceptable oral bioavailability, which is strongly dependent on solubility in the aqueous medium of the gastrointestinal tract. Various solutions to the challenge of low oral bioavailability have been proposed in the art. For example, Sharma & Joshi (2007) *Asian Journal of Pharmaceutics* 1(1):9-19 discuss various solubility enhancement strategies in preparing solid dispersions. A solvent evaporation method for preparing solid dispersions is described therein, mentioning as an example a solid dispersion of etoricoxib, prepared by a process that includes dissolving polyethylene glycol (PEG), polyvinylpyrrolidone (PVP or povidone) and the active ingredient in 2-propanol.

To enhance clinical utility of an inhibitor of protein kinases, for example as a chemotherapeutic in cancer patients, a solid dosage form with acceptable oral bioavailability would be highly desirable. Such a dosage form, and a regimen for oral administration thereof, would represent an important advance in treatment of many types of cancer, and would more readily enable combination therapies with other chemotherapeutics.

SUMMARY OF THE INVENTION

There is now provided a solid dispersion product comprising N-(4-{4-amino-7-[1-(2-hydroxyethyl)-1H-pyrazol-4-yl]thieno[3,2-c]pyridin-3-yl}phenyl)-N'-(3-fluorophenyl)urea or a salt thereof, at least one pharmaceutically acceptable water-soluble polymeric carrier, and at least one pharmaceutically acceptable surfactant.

There is further provided a solid dispersion product comprising N-(4-{4-amino-7-[1-(2-hydroxyethyl)-1H-pyrazol-4-yl]thieno [3,2-c]pyridin-3-yl}phenyl)-N'-(3-fluorophenyl)urea or a salt thereof, at least one acid, at least one pharmaceutically acceptable water-soluble polymeric carrier, and at least one pharmaceutically acceptable surfactant.

There is further provided a solid dispersion product comprising N-(4-{4-amino-7-[1-(2-hydroxyethyl)-1H-pyrazol-4-yl]thieno[3,2-c]pyridin-3-yl}phenyl)-N'-(3-fluorophenyl)urea, at least one acid, at least one pharmaceutically acceptable water-soluble polymeric carrier, and at least one pharmaceutically acceptable surfactant.

There is further provided a solid orally deliverable dosage form comprising such a solid dispersion product, optionally together with one or more additional excipients.

There is still further provided a process for preparing a solid dispersion product as described above. This process comprises:

(a) forming a solution comprising (i) N-(4-{4-amino-7-[1-(2-hydroxyethyl)-1H-pyrazol-4-yl]thieno[3,2-c]pyridin-3-yl}phenyl)-N'-(3-fluorophenyl)urea or salt thereof, (ii) a pharmaceutically acceptable acid, (iii) at least one pharmaceutically acceptable water-soluble polymeric carrier, (iv) at least one pharmaceutically acceptable surfactant, and (v) at least one suitable solvent; and (b) removing the at least one solvent to provide a solid dispersion comprising the at least polymeric carrier, the at least one surfactant, the at least one acid, and having N-(4-{4-amino-7-[1-(2-hydroxyethyl)-1H-pyrazol-4-yl]thieno[3,2-c]pyridin-3-yl}phenyl)-N'-(3-fluorophenyl)urea dispersed in an essentially non-crystalline form therein.

There is still further provided a solid dispersion prepared by the process described above.

There is still further provided a method for treating cancer comprising orally administering to a subject having the disease a therapeutically effective amount of a solid dispersion as described above, or one or more solid dosage forms comprising such a dispersion.

There is further provided a solid dispersion product comprising a kinase inhibitor, at least one pharmaceutically acceptable water-soluble polymeric carrier, and at least one pharmaceutically acceptable surfactant, wherein the solid dispersion (a) remains amorphous for at least 1 month under open storage at 25° C. and 75% RH and (b) exhibits a glass transition temperature at 75% RH of less than or equal to 15° C. Preferably, the kinase inhibitor is N-(4-{4-amino-7-[1-(2-hydroxyethyl)-1H-pyrazol-4-yl]thieno[3,2-c]pyridin-3-yl}phenyl)-N'-(3-fluorophenyl)urea or a pharmaceutically acceptable salt thereof.

Additional embodiments of the invention, including more particular aspects of those provided above, will be found in, or will be evident from, the detailed description that follows.

DETAILED DESCRIPTION

A solid dispersion in accordance with the present disclosure comprises N-(4-{4-amino-7-[1-(2-hydroxyethyl)-1H-pyrazol-4-yl]thieno[3,2-c]pyridin-3-yl}phenyl)-N'-(3-fluorophenyl)urea or a pharmaceutically acceptable salt thereof in an essentially non-crystalline or amorphous form, which is usually more soluble than the crystalline form. The term "solid dispersion" herein encompasses systems having small solid-state particles of one phase dispersed in another solid-state phase. More particularly, the present solid dispersions comprise N-(4-{4-amino-7-[1-(2-hydroxyethyl)-1H-pyrazol-4-yl]thieno[3,2-c]pyridin-3-yl}phenyl)-N'-(3-fluorophenyl)urea dispersed in an inert carrier.

An "amorphous form" refers to a particle without definite structure, i.e., lacking crystalline structure.

The term "essentially non-crystalline" herein means that no more than about 5%, for example no more than about 2%, or no more than about 1% crystallinity is observed by X-ray diffraction analysis. In a particular embodiment, no detectable crystallinity is observed by one or both of X-ray diffraction analysis or polarization microscopy.

N-(4-{4-amino-7-[1-(2-hydroxyethyl)-1H-pyrazol-4-yl]thieno[3,2-c]pyridin-3-yl}phenyl)-N'-(3-fluorophenyl)urea, including salts thereof, typically have very low solubility in water, for example less than about 100 µg/ml, in most cases less than about 30 µg/ml. The present invention can be especially advantageous for drugs that are essentially insoluble in water, i.e., having a solubility of less than about 10 µg/ml, since a process of the invention increases the apparent solubility of such a poorly-soluble active ingredient. Examples of such active ingredients are, for example, Biopharmaceutics Classification System (BCS) Class IV drug substances that are characterized by low solubility and low permeability (see "Waiver of in vivo bioavailability and bioequivalence studies for immediate-release solid oral dosage forms based on a biopharmaceutics classification system", U.S. Department of Health and Human Services, Food and Drug Administration, Center for Drug Evaluation and Research (CDER), August 2000). It will be recognized that aqueous solubility of many compounds is pH-dependent; in the case of such compounds the solubility of interest herein is at a physiologically relevant pH, for example a pH of about 1 to about 8. Thus, in various embodiments, the drug has a solubility in water, at least at one point in a pH range from about 1 to about 8, of less than about 100 µg/ml, for example less than about 30 µg/ml, or less than about 10 µg/ml. Illustratively, N-(4-{4-amino-7-[1-(2-hydroxyethyl)-1H-pyrazol-4-yl]thieno[3,2-c]pyridin-3-yl}phenyl)-N'-(3-fluorophenyl)urea has a solubility in water of less than 30 ng/ml at pH 7.4.

Solid dispersions of the present invention comprise as active ingredient N-(4-{4-amino-7-[1-(2-hydroxyethyl)-1H-pyrazol-4-yl]thieno[3,2-c]pyridin-3-yl}phenyl)-N'-(3-fluorophenyl)urea or a pharmaceutically acceptable salt thereof. Optionally they may further comprise a second active ingredient, for example a therapeutic agent useful in combination therapy as indicated herein below.

The active ingredient N-(4-{4-amino-7-[1-(2-hydroxyethyl)-1H-pyrazol-4-yl]thieno[3,2-c]pyridin-3-yl}phenyl)-N'-(3-fluorophenyl)urea for use in this invention can be crystalline or amorphous in its undispersed state.

The active ingredient N-(4-{4-amino-7-[1-(2-hydroxyethyl)-1H-pyrazol-4-yl]thieno[3,2-c]pyridin-3-yl}phenyl)-

N'-(3-fluorophenyl)urea for use in this invention can be in salt form or the non-salt free base.

For example, the active ingredient N-(4-{4-amino-7-[1-(2-hydroxyethyl)-1H-pyrazol-4-yl]thieno[3,2-c]pyridin-3-yl}phenyl)-N'-(3-fluorophenyl)urea may form acid addition salts. Acid addition salts are those derived from reaction of a N-(4-{4-amino-7-[1-(2-hydroxyethyl)-1H-pyrazol-4-yl]thieno[3,2-c]pyridin-3-yl}phenyl)-N'-(3-fluorophenyl)urea with an acid. For example, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate and undecanoate salts of N-(4-{4-amino-7-[1-(2-hydroxyethyl)-1H-pyrazol-4-yl]thieno[3,2-c]pyridin-3-yl}phenyl)-N'-(3-fluorophenyl)urea can be used in a solid dispersion of the invention.

N-(4-{4-amino-7-[1-(2-hydroxyethyl)-1H-pyrazol-4-yl]thieno[3,2-c]pyridin-3-yl}phenyl)-N'-(3-fluorophenyl)urea is prepared, illustratively, as described in Example 1 of above-cited U.S. patent application Ser. No. 12/632,183, the entire disclosure of which is incorporated by reference herein.

N-(4-{4-amino-7-[1-(2-hydroxyethyl)-1H-pyrazol-4-yl]thieno[3,2-c]pyridin-3-yl}phenyl)-N'-(3-fluorophenyl)urea is present in a solid dispersion of the invention in an amount that can be therapeutically effective when the composition is administered to a subject in need thereof according to an appropriate regimen. Dosage amounts are expressed herein as parent-compound-equivalent (free base equivalent) amounts unless the context requires otherwise. Typically, a unit dose (the amount administered at a single time), which can be administered at an appropriate frequency, e.g., twice daily to once weekly, is about 10 to about 1,000 mg, depending on the compound in question. Where frequency of administration is once daily (q.d.), unit dose and daily dose are the same. Illustratively, the unit dose is typically about 25 to about 1,000 mg, more typically about 50 to about 500 mg, for example about 50, about 100, about 150, about 200, about 250, about 300, about 350, about 400, about 450 or about 500 mg. Where the dosage form comprises a capsule shell enclosing the solid dispersion, a unit dose can be deliverable in a single capsule or a plurality of capsules, most typically 1 to about 10 capsules.

The higher the unit dose, the more desirable it becomes to prepare a solid dispersion having a relatively high concentration of the drug therein. Typically, the concentration of drug in the solid dispersion is at least about 1%, e.g., about 1% to about 50%, by free base equivalent weight, but lower and higher concentrations can be acceptable or achievable in specific cases. The drug concentration in various embodiments is at least about 1%, e.g., about 1% to about 40%, or at least about 5%, e.g., about 5% to about 15%, or about 8%, e.g., about 8% to about 12% by free base equivalent weight.

In some embodiments of the invention, the solid dispersion product of the invention comprises at least one acid. The at least one acid is selected from the group consisting of citric acid, tartaric acid, succinic acid, malic acid, acetic acid, maleic acid, malonic acid, ascorbic acid, lactic acid, sulfuric acid, phosphoric acid, hydrochloric acid, hydrobromic acid, methanesulfonic acid, benznesulfonic acid, toluenesulfonic acid, ethanedisulfonic acid, naphthalenesulfonic acid, and 1-hydroxy-2-napthoic acid. In a preferred embodiment, the at least one acid is citric acid.

The at least one acid typically constitute in total about 0.1 to about 10 equivalents with respect to N-(4-{4-amino-7-[1-(2-hydroxyethyl)-1H-pyrazol-4-yl]thieno[3,2-c]pyridin-3-yl}phenyl)-N'-(3-fluorophenyl)urea, e.g., about 0.1 or more, about 0.5 or more, about 1 or more, about 2 or more, or about 5 or more equivalents.

The major component of the matrix of a solid dispersion product is a polymer that is hydrophilic or water-soluble at least in a part of the pH scale, more particularly at a pH occurring in the gastrointestinal (GI) tract, or a combination of such polymers. A polymer or polymer mixture useful herein is solid at ambient temperature and, in the interests of good storage stability at a range of temperatures, should remain solid even at the highest temperatures typically experienced during storage, transport and handling of the product. A useful property of a polymer determining its usefulness herein is therefore its glass transition temperature ($T_g$). Suitable water-soluble polymers include, but are not limited to, those having a $T_g$ of at least about 50° C., more particularly about 80° C. to about 180° C. Methods for determining $T_g$ values of organic polymers are described for example in Sperling, ed. (1992) *Introduction To Physical Polymer Science*, 2nd edition, John Wiley & Sons, Inc.

Non-limiting examples of polymeric carriers useful herein include:

homopolymers and copolymers of N-vinyl lactams, especially homopolymers and copolymers of N-vinyl pyrrolidone, e.g., the homopolymer polyvinylpyrrolidone (PVP or povidone, e.g., Kollidon® 12 PF or equivalent thereof, Kollidon® 17 PF or equivalent thereof, Kollidon® 25 or equivalent thereof, Kollidon® 30 or equivalent thereof, Kollidon® 90 F or equivalent thereof) and copolymers such as those comprising monomers of N-vinyl pyrrolidone and vinyl acetate (copovidone) or N-vinyl pyrrolidone and vinyl propionate;

cellulose esters and cellulose ethers, in particular methylcellulose, ethylcellulose, (hydroxyalkyl)celluloses such as hydroxypropylcellulose, (hydroxyalkyl)alkyl-celluloses such as hydroxypropylmethylcellulose (HPMC or hypromellose, e.g., Methocel™ E3 or equivalent thereof, Methocel™ E5 or equivalent thereof, Methocel™ E6 or equivalent thereof, Methocel™ E15 or equivalent thereof, Methocel™ K3 or equivalent thereof,), cellulose phthalates and succinates such as cellulose acetate phthalate, hydroxypropylmethylcellulose phthalate, hydroxypropylmethylcellulose succinate and hydroxypropylmethylcellulose acetate succinate (HPMC-AS);

high molecular weight polyalkylene oxides such as polyethylene oxide, polypropylene oxide and copolymers of ethylene oxide and propylene oxide (poloxamers);

polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly (hydroxyalkyl acrylates) and poly(hydroxyalkyl methacrylates);

polyacrylamides;

vinyl acetate polymers such as copolymers of vinyl acetate and crotonic acid, partially hydrolyzed polyvinyl acetate (also referred to as partially saponified "polyvinyl alcohol") and polyvinyl alcohol;

oligo- and polysaccharides such as carrageenans, galactomannans and xanthan gum;

and mixtures of two or more thereof.

In one embodiment, the solid dispersion matrix comprises one or more polymeric carriers selected from the group consisting of polyvinylpyrrolidone, hydroxypropyl methylcellulose, and mixtures thereof. A particular example of a useful copovidone is one consisting of about 60% N-vinyl pyrrolidone and about 40% vinyl acetate monomers. A particular example of a useful povidone is one having a K-value (a measure of viscosity of an aqueous solution of the povidone) of about 30.

One or more polymeric carriers typically constitute in total about 20% to about 90%, for example about 40% to about 85%, by weight of the solid dispersion.

Upon oral administration and exposure to GI fluid, it is believed without being bound by theory that, through interplay between the polymeric carrier and a surfactant component of the solid dispersion, a suitable release rate and inhibition of crystallization or recrystallization of the active ingredient are provided, thereby permitting bioabsorption.

Particularly useful as surfactants herein are pharmaceutically acceptable non-ionic surfactants, especially those having a hydrophilic-lipophilic balance (HLB) value of about 12 to about 18, for example about 13 to about 17, or about 14 to about 16. The HLB system (see Fiedler (2002) *Encyclopedia of Excipients*, 5th edition, Aulendorf: ECV-Editio-Cantor-Verlag) attributes numeric values to surfactants, with lipophilic substances receiving lower HLB values and hydrophilic substances receiving higher HLB values.

Non-limiting examples of non-ionic surfactants useful herein include:
- polyoxyethylene castor oil derivatives such as PEG-35 castor oil (e.g., Cremophor® EL of BASF Corp. or equivalent product), PEG-40 hydrogenated castor oil (e.g., Cremophor® RH40 or equivalent product) and PEG-60 hydrogenated castor oil (e.g., Cremophor® RH 60 or equivalent product);
- fatty acid monoesters of sorbitan, for example sorbitan monooleate (e.g., Span® 80 or equivalent product), sorbitan monostearate (e.g., Span® 60 or equivalent product), sorbitan monopalmitate (e.g., Span® 40 or equivalent product) and sorbitan monolaurate (e.g., Span® 20 or equivalent product);
- fatty acid monoesters of polyoxyethylene sorbitan (polysorbates) such as PEG-20 sorbitan monooleate (polysorbate 80, e.g., Tween® 80 or equivalent product) PEG-20 sorbitan monostearate (polysorbate 60, e.g., Tween® 60 or equivalent product), PEG-20 sorbitan monopalmitate (polysorbate 40, e.g., Tween® 40 or equivalent product), or PEG-20 sorbitan monolaurate (polysorbate 20, e.g., Tween™ 20 or equivalent product);
- poloxamers such as poloxamer 124, poloxamer 188, poloxamer 237, poloxamer 388 or poloxamer 407;
- polyethylene glycol glycerides composed of mono-, di- and triglycerides and mono- and diesters of polyethylene glycol (e.g. Gelucire® 44/14 or equivalent product and Gelucire® 50/13 or equivalent product)
- α-tocopheryl polyethylene glycol succinate (TPGS or vitamin E polyethylene glycol succinate, see U.S. National Formulary);

and mixtures of two or more thereof.

One or more surfactants typically constitute in total about 2% to about 40%, for example about 5% to about 30%, by weight of the solid dispersion.

The solid dispersions of the present invention are stable, i.e., the solid dispersion remains amorphous. It is critical that the amorphous solid dispersions do not change form over time and potentially affect the drug product's performance. Therefore, in yet another embodiment, there is further provided a solid dispersion product comprising a kinase inhibitor, at least one pharmaceutically acceptable water-soluble polymeric carrier, and at least one pharmaceutically acceptable surfactant, wherein the solid dispersion (a) remains amorphous for at least 1 month under open storage at 25° C. and 75% RH and (b) exhibits a glass transition temperature at 75% RH of less than or equal to 15° C. Preferably, the kinase inhibitor is N-(4-{4-amino-7-[1-(2-hydroxyethyl)-1H-pyrazol-4-yl]thieno[3,2-c]pyridin-3-yl}phenyl)-N'-(3-fluorophenyl)urea or a pharmaceutically acceptable salt thereof.

A dosage form of the invention can consist of, or consist essentially of, a solid dispersion as described above. However, in some embodiments a dosage form contains additional excipients and requires additional processing of the solid dispersion. For example, the solid dispersion can be ground to a powder and filled into a capsule shell or molded or compressed to form a tablet, with additional excipients as may be conventionally used in such dosage forms.

Thus orally deliverable solid dosage forms of the invention include but are not limited to capsules, dragees, granules, pills, powders and tablets. Excipients commonly used to formulate such dosage forms include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, preservatives, propellants, releasing agents, sterilizing agents, sweeteners, solubilizers and mixtures thereof. Examples of specific excipients include agar, alginic acid, aluminum hydroxide, benzyl benzoate, 1,3-butylene glycol, castor oil, cellulose, cellulose acetate, cocoa butter, corn starch, corn oil, cottonseed oil, ethanol, ethyl acetate, ethyl carbonate, ethyl cellulose, ethyl laureate, ethyl oleate, gelatin, germ oil, glucose, glycerol, groundnut oil, isopropanol, isotonic saline, lactose, magnesium hydroxide, magnesium stearate, malt, olive oil, peanut oil, potassium phosphate salts, potato starch, propylene glycol, talc, tragacanth, water, safflower oil, sesame oil, sodium carboxymethyl cellulose, sodium lauryl sulfate, sodium phosphate salts, soybean oil, sucrose, tetrahydrofurfuryl alcohol, and mixtures thereof.

In one embodiment, the orally deliverable solid dosage form of the invention is a tablet containing solid dispersion powder, filler, disintegrant, glidant and lubricant. In another embodiment, the tablet contains 50% by weight of the solid dispersion powder.

A process for preparing a solid dispersion as described above comprises forming a solution comprising N-(4-{4-amino-7-[1-(2-hydroxyethyl)-1H-pyrazol-4-yl]thieno[3,2-c]pyridin-3-yl}phenyl)-N'-(3-fluorophenyl)urea or a salt thereof, the acid, the polymeric carrier and the surfactant in at least one suitable solvent; and removing the solvent to provide the solid dispersion.

Alternatively, a process for preparing a solid dispersion as described above comprises forming a solution comprising N-(4-{4-amino-7-[1-(2-hydroxyethyl)-1H-pyrazol-4-yl]thieno[3,2-c]pyridin-3-yl}phenyl)-N'-(3-fluorophenyl)urea or a salt thereof, the polymeric carrier and the surfactant in at least one suitable solvent; and removing the solvent to provide the solid dispersion.

In yet another embodiment, a process for preparing a solid dispersion as described above comprises forming a solution comprising N-(4-{4-amino-7-[1-(2-hydroxyethyl)-1H-pyrazol-4-yl]thieno[3,2-c]pyridin-3-yl}phenyl)-N'-(3-fluorophenyl)urea, the acid, the polymeric carrier and the surfactant in at least one suitable solvent; and removing the solvent to provide the solid dispersion.

In the forming step, the various components can be added in any order. For example, each ingredient can be added to the solvent separately and then dissolved therein. Alternatively, the polymeric carrier and/or surfactant can be pre-mixed with the N-(4-{4-amino-7-[1-(2-hydroxyethyl)-1H-pyrazol-4-yl]thieno[3,2-c]pyridin-3-yl}phenyl)-N'-(3-fluorophenyl)urea, and the resulting mixture then added to the solvent or the solvent added to the resulting mixture. Alternatively, N-(4-{4-amino-7-[1-(2-hydroxyethyl)-1H-pyrazol-4-yl]thieno[3,2-c]pyridin-3-yl}phenyl)-N'-(3-fluorophenyl)urea and the acid can be added to the at least one solvent, then add the polymeric carrier and surfactant.

In principle any solvent can be used so long as it is effective to dissolve the active ingredient, polymer carrier and surfactant. Non-limiting examples of solvents that can be useful include methanol, ethanol, acetone, tetrahydrofuran, water and mixtures thereof. In a preferred embodiment, a combination of an aqueous solvent and a water-miscible organic solvent is used. Preferably, the components are dissolved in a mixture of water and acetone or a mixture of water and tetrahydrofuran.

Solvent removal can be accomplished using heat, vacuum or a combination thereof. If heat is used, it is generally preferable to avoid exceeding the glass transition temperature ($T_g$) of the polymeric matrix. For most purposes heating at a temperature of about 50° C. to about 80° C., for example about 55° C. to about 75° C., will be found suitable. After solvent removal, the resulting product is cooled (if necessary) to ambient temperature.

Further process details can be found in the illustrative processes of Example 1 below.

The terms "orally deliverable", "oral administration" and "orally administered" herein refer to administration to a subject per os (p.o.), that is, administration wherein the composition is immediately swallowed, for example with the aid of a suitable volume of water or other potable liquid. "Oral administration" is distinguished herein from intraoral administration, e.g., sublingual or buccal administration or topical administration to intraoral tissues such as periodontal tissues, that does not involve immediate swallowing of the composition.

The invention provides a solid dispersion or dosage form having acceptable bioabsorption when administered orally. Such bioabsorption can be evidenced, for example, by the pharmacokinetic (PK) profile of the solid dispersion or dosage form, more particularly by the $C_{max}$ or AUC, for example $AUC_{0-24}$ or $AUC_{0-\infty}$ at a particular dose or over a range of doses. Illustratively, bioavailability can be expressed as a percentage, for example using the parameter F, which computes AUC for oral delivery of a test composition as a percentage of AUC for intravenous (i.v.) delivery of the drug in a suitable solvent, taking into account any difference between oral and i.v. doses.

Bioavailability can be determined by PK studies in humans or in any suitable model species. For present purposes, a dog model, as illustratively described in Example 2 below, is generally suitable. In various illustrative embodiments, where the drug is N-(4-{4-amino-7-[1-(2-hydroxyethyl)-1H-pyrazol-4-yl]thieno[3,2-c]pyridin-3-yl}phenyl)-N'-(3-fluorophenyl)urea, compositions of the invention exhibit oral bioavailability of at least about 15%, at least about 20%, at least about 25% or at least about 30%, up to or exceeding about 50%, in a dog model, when administered as a single dose of about 2.5 to about 50 mg/kg to fasting or non-fasting animals.

Compositions embraced herein, including compositions described generally or with specificity herein, are useful for orally delivering N-(4-{4-amino-7-[1-(2-hydroxyethyl)-1H-pyrazol-4-yl]thieno[3,2-c]pyridin-3-yl}phenyl)-N'-(3-fluorophenyl)urea to a subject. Accordingly, a method of the invention for delivering such a drug to a subject comprises orally administering a composition as described above.

The subject can be human or non-human (e.g., a farm, zoo, work or companion animal, or a laboratory animal used as a model) but in an important embodiment the subject is a human patient in need of the drug, for example to treat cancer. A human subject can be male or female and of any age, but is typically an adult.

The composition is normally administered in an amount providing a therapeutically effective daily dose of the drug. The term "daily dose" herein means the amount of drug administered per day, regardless of the frequency of administration. For example, if the subject receives a unit dose of 150 mg twice daily, the daily dose is 300 mg. Use of the term "daily dose" will be understood not to imply that the specified dosage amount is necessarily administered once daily. However, in a particular embodiment the dosing frequency is once daily (q.d.), and the daily dose and unit dose are in this embodiment the same thing.

What constitutes a therapeutically effective dose depends on the particular compound, the subject (including species and body weight of the subject), the disease (e.g., the particular type of cancer) to be treated, the stage and/or severity of the disease, the individual subject's tolerance of the compound, whether the compound is administered in monotherapy or in combination with one or more other drugs, e.g., other chemotherapeutics for treatment of cancer, and other factors. Thus the daily dose can vary within wide margins, for example from about 10 to about 1,000 mg. Greater or lesser daily doses can be appropriate in specific situations. It will be understood that recitation herein of a "therapeutically effective" dose herein does not necessarily require that the drug be therapeutically effective if only a single such dose is administered; typically therapeutic efficacy depends on the composition being administered repeatedly according to a regimen involving appropriate frequency and duration of administration. It is strongly preferred that, while the daily dose selected is sufficient to provide benefit in terms of treating the cancer, it should not be sufficient to provoke an adverse side-effect to an unacceptable or intolerable degree. A suitable therapeutically effective dose can be selected by the physician of ordinary skill without undue experimentation based on the disclosure herein and on art cited herein, taking into account factors such as those mentioned above. The physician may, for example, start a cancer patient on a course of therapy with a relatively low daily dose and titrate the dose upwards over a period of days or weeks, to reduce risk of adverse side-effects.

Illustratively, suitable doses of N-(4-{4-amino-7-[1-(2-hydroxyethyl)-1H-pyrazol-4-yl]thieno[3,2-c]pyridin-3-yl}phenyl)-N'-(3-fluorophenyl)urea are generally about 10 to about 1,000 mg/day, more typically about 50 to about 500 mg/day or about 200 to about 400 mg/day, for example about 50, about 100, about 150, about 200, about 250, about 300, about 350, about 400, about 450 or about 500 mg/day, administered at an average dosage interval of 3 to 10 days, or about 4 to 8 days, or about 7 days.

Where the composition is in the form of a capsule, one to a small plurality of capsules can be swallowed whole, typically with the aid of water or other imbibable liquid to help the swallowing process. Suitable capsule shell materials include, without limitation, gelatin (in the form of hard gelatin capsules or soft elastic gelatin capsules), starch, carrageenan and HPMC.

As compositions of the present invention are believed to exhibit only a minor food effect, administration according to the present embodiment can be with or without food, i.e., in a non-fasting or fasting condition. It is generally preferred to administer the present compositions to a non-fasting patient.

Compositions of the invention are suitable for use in monotherapy or in combination therapy, for example with other chemotherapeutics or with ionizing radiation. A particular advantage of the present invention is that it permits once-daily oral administration, a regimen which is convenient for the patient who is undergoing treatment with other orally administered drugs on a once-daily regimen. Oral administration is easily accomplished by the patient him/herself or by a caregiver in the patient's home; it is also a convenient route of administration for patients in a hospital or residential care setting.

A composition of the invention, for example such a composition comprising N-(4-{4-amino-7-[1-(2-hydroxyethyl)-1H-pyrazol-4-yl]thieno[3,2-c]pyridin-3-yl}phenyl)-N'-(3-fluorophenyl)urea, can be administered in combination therapy with one or more therapeutic agents that include, but are not limited to, alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1 inhibitors), activators of a death receptor pathway, Bcr-Abl kinase inhibitors, BiTE (bi-specific T-cell engager) antibodies, antibody-drug conjugates, biological response modifiers, cyclin-dependent kinase (CDK) inhibitors, cell cycle inhibitors, cyclooxygenase-2 (COX-2) inhibitors, dual variable domain binding proteins (DVDs), human epidermal growth factor receptor 2 (ErbB2 or HER/2neu) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAPs), intercalating antibiotics, kinase inhibitors, kinesin inhibitors, JAK2 inhibitors, mammalian target of rapamycin (mTOR) inhibitors, microRNAs, mitogen-activated extracellular signal-regulated kinase (MEK) inhibitors, multivalent binding proteins, non-steroidal anti-inflammatory drugs (NSAIDs), poly-ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids, deltoids, plant alkaloids, small inhibitory ribonucleic acids (siRNAs), topoisomerase inhibitors, ubiquitin ligase inhibitors, and the like.

BiTE antibodies are bi-specific antibodies that direct T-cells to attack cancer cells by simultaneously binding the two cells. The T-cell then attacks the target cancer cell. Examples of BiTE antibodies include, but are not limited to, adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (Sutton et al. (1997) *J. Immunol.* 158:5783-5790).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263 or ABT-737 in various tumor cell lines (Tse et al. (2008) *Cancer Res.* 68:3421-3428 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins comprising two or more antigen binding sites. Such DVDs may be monospecific (i.e., capable of binding one antigen) or multispecific (i.e., capable of binding two or more antigens). DVD binding proteins comprising two heavy-chain DVD polypeptides and two light-chain DVD polypeptides are referred to as DVD Ig's. Each half of a DVD Ig comprises a heavy-chain DVD polypeptide, a light-chain DVD polypeptide, and two antigen binding sites. Each binding site comprises a heavy-chain variable domain and a light-chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, Cloretazine™ (laromustine, VNP 40101M), cyclophosphamide, dacarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include epidermal growth factor receptor (EGFR) inhibitors, endothelial-specific receptor tyrosine kinase (Tie-2) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include Alimta™ (pemetrexed disodium, LY231514, MTA), 5-azacitidine, Xeloda™ (capecitabine), carmofur, Leustat™ (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethenylcytidine, fludarabine, 5-fluorouracil (5-FU) alone or in combination with leucovorin, Gemzar™ (gemcitabine), hydroxyurea, Alkeran™ (melphalan), mercaptopurine, 6-mercaptopurine riboside, methotrexate, mycophenolic acid, nelarabine, nolatrexed, ocfosfate, pelitrexol, pentostatin, raltitrexed, ribavirin, S-1, triapine, trimetrexate, TS-1, tiazofurin, tegafur, vidarabine, UFT and the like.

Antivirals include ritonavir, hydroxychloroquine and the like.

Aurora kinase inhibitors include AZD-1152, MLN-8054, VX-680, aurora A-specific kinase inhibitors, aurora B-specific kinase inhibitors, pan-aurora kinase inhibitors and the like.

Bcl-2 family protein inhibitors other than ABT-263 or compounds of Formula I herein include AT-101 ((-)gossypol), Genasense™ Bcl-2-targeting antisense oligonucleotide (G3139 or oblimersen), IPI-194, IPI-565, N-(4-(4-((4'-chloro (1,1'-biphenyl)-2-yl)methyl) piperazin-1-yl)benzoyl)-4-(((1R)-3-(dimethylamino)-1-((phenylsulfanyl)methyl)propyl)amino)-3-nitrobenzenesulfonamide) (ABT-737), GX-070 (obatoclax) and the like Bcr-Abl kinase inhibitors include dasatinib (BMS-354825), Gleevec™ (imatinib) and the like.

CDK inhibitors include AZD-5438, BMI-1040, BMS-387032, CVT-2584, flavopyridol, GPC-286199, MCS-5A, PD0332991, PHA-690509, seliciclib (CYC-202 or R-roscovitine), ZK-304709 and the like.

COX-2 inhibitors include ABT-963, Arcoxia™ (etoricoxib), Bextra™ (valdecoxib), BMS-347070, Celebrex™ (celecoxib), COX-189 (lumiracoxib), CT-3, Deramaxx™ (deracoxib), JTE-522, 4-methyl-2-(3,4-dimethylphenyl)-1-(4-sulfamoylphenyl)-1H-pyrrole, MK-663 (etoricoxib), NS-398, parecoxib, RS-57067, SC-58125, SD-8381, SVT-2016, S-2474, T-614, Vioxx™ (rofecoxib) and the like.

EGFR inhibitors include ABX-EGF, anti-EGFR immunoliposomes, EGF-vaccine, EMD-7200, Erbitux™ (cetuximab), HR3, IgA antibodies, Iressa™ (gefitinib), Tarceva™ (erlotinib or OSI-774), TP-38, EGFR fusion protein, Tykerb™ (lapatinib) and the like.

ErbB2 receptor inhibitors include CP-724714, CI-1033 (canertinib), Herceptin™ (trastuzumab), Tykerb™ (lapatinib), Omnitarg™ (2C4, petuzumab), TAK-165, GW-572016 (ionafamib), GW-282974, EKB-569, PI-166, dHER2 (HER2 vaccine), APC-8024 (HER2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17AAG, CNF-101, CNF-1010, CNF-2024, 17-DMAG, geldanamycin, IPI-504, KOS-953, Mycograb™ (human recombinant antibody to HSP-90), nab-17AAG, NCS-683664, PU24FC1, PU-3, radicicol, SNX-2112, STA-9090, VER-49009 and the like.

Inhibitors of apoptosis proteins include HGS-1029, GDC-0145, GDC-0152, LCL-161, LBW-242 and the like.

Antibody-drug conjugates include anti-CD22-MC-MMAF, anti-CD22-MC-MMAE, anti-CD22-MCC-DM1, CR-011-vcMMAE, PSMA-ADC, MEDI-547, SGN-19A, SGN-35, SGN-75 and the like.

Activators of death receptor pathway include TRAIL and antibodies or other agents that target TRAIL or death receptors (e.g., DR4 and DR5) such as apomab, conatumumab, ETR2-ST01, GDC0145 (lexatumumab), HGS-1029, LBY-135, PRO-1762, trastuzumab and the like.

Kinesin inhibitors include Eg5 inhibitors such as AZD-4877 and ARRY-520, CENPE inhibitors such as GSK-923295A, and the like.

JAK2 inhibitors include CEP-701 (lesaurtinib), XL019, NCB-018424 and the like.

MEK inhibitors include ARRY-142886, ARRY-438162, PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30 and Torin 1, and the like.

Non-steroidal anti-inflammatory drugs include Amigesic™ (salsalate), Dolobid™ (diflunisal), Motrin™ (ibuprofen), Orudis™ (ketoprofen), Relafen™ (nabumetone), Feldene™ (piroxicam), ibuprofen cream, Aleve™ and Naprosyn™ (naproxen), Voltaren™ (diclofenac), Indocin™ (indomethacin), Clinoril™ (sulindac), Tolectin™ (tolmetin), Lodine™ (etodolac), Toradol™ (ketorolac), Daypro™ (oxaprozin) and the like.

PDGFR inhibitors include CP-673451, CP-868596 and the like.

Platinum chemotherapeutics include cisplatin, Eloxatin™ (oxaliplatin), eptaplatin, lobaplatin, nedaplatin, Paraplatin™ (carboplatin), picoplatin, satraplatin and the like.

Polo-like kinase inhibitors include BI-2536 and the like.

Phosphoinositide-3 kinase inhibitors include wortmannin, LY-294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include Avastin™ (bevacizumab), ABT-869, AEE-788, Angiozyme™ (a ribozyme that inhibits angiogenesis (Ribozyme Pharmaceuticals (Boulder, Colo.) and Chiron (Emeryville, Calif.)), axitinib (AG-13736), AZD-2171, CP-547632, IM-862, Macugen™ (pegaptanib), Nexavar™ (sorafenib, BAY43-9006), pazopanib (GW-786034), vatalanib (PTK-787 or ZK-222584), Sutent™ (sunitinib or SU-11248), VEGF trap, Zactima™ (vandetanib or ZD-6474) and the like.

Antibiotics include intercalating antibiotics such as aclarubicin, actinomycin D, amrubicin, annamycin, Adriamycin™ (doxorubicin), Blenoxane™ (bleomycin), daunorubicin, Caelyx™ and Myocet™ (liposomal doxorubicin), elsamitrucin, epirubicin, glarubicin, idarubicin, mitomycin C, nemorubicin, neocarzinostatin, peplomycin, pirarubicin, rebeccamycin, stimalamer, streptozocin, Valstar™ (valrubicin), zinostatin and the like.

Topoisomerase inhibitors include aclarubicin, 9-aminocamptothecin, amonafide, amsacrine, becatecarin, belotecan, BN-80915, Camptosar™ (irinotecan hydrochloride), camptothecin, Cardioxane™ (dexrazoxane), diflomotecan, edotecarin, Ellence™ and Pharmorubicin™ (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include Avastin™ (bevacizumab), CD40-specific antibodies, chTNT-1/B, denosumab, Erbitux™ (cetuximab), Humax-CD4™ (zanolimumab), IGF1R-specific antibodies, lintuzumab, Panorex™ (edrecolomab), Rencarex™ (WX G250), Rituxan™ (rituximab), ticilimumab, trastuzumab, CD20 antibodies types I and II and the like.

Hormonal therapies include Arimidex™ (anastrozole), Aromasin™ (exemestane), arzoxifene, Casodex™ (bicalutamide), Cetrotide™ (cetrorelix), degarelix, deslorelin, Desopan™ (trilostane), dexamethasone, Drogenil™ (flutamide), Evista™ (raloxifene), Afema™ (fadrozole), Fareston™ (toremifene), Faslodex™ (fulvestrant), Femara™ (letrozole), formestane, glucocorticoids, Hectorol™ (doxercalciferol), Renagel™ (sevelamer carbonate), lasofoxifene, leuprolide acetate, Megace™ (megestrol), Mifeprex™ (mifepristone), Nilandron™ (nilutamide), tamoxifen including Nolvadex™ (tamoxifen citrate), Plenaxis™ (abarelix), prednisone, Propecia™ (finasteride), rilostane, Suprefact™ (buserelin), luteinizing hormone releasing hormone (LHRH) including Trelstar™ (triptorelin), histrelin including Vantas™ (histrelin implant), Modrastane™ (trilostane), Zoladex™ (goserelin) and the like.

Deltoids and retinoids include seocalcitol (EB1089 or CB1093), lexacalcitol (KH1060), fenretinide, Panretin™ (alitretinoin), tretinoin including Atragen™ (liposomal tretinoin), Targretin™ (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include vincristine, vinblastine, vindesine, vinorelbine and the like.

Proteasome inhibitors include Velcade™ (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, Actimmune™ (interferon gamma-1b), interferon gamma-n1, combinations thereof and the like. Other agents include Alfaferone (IFN-α), BAM-002 (oxidized glutathione), Beromun™ (tasonermin), Bexxar™ (tositumomab), Campath™ (alemtuzumab), CTLA4 (cytotoxic lymphocyte antigen 4), dacarbazine, denileukin, epratuzumab, Granocyte™ (lenograstim), lentinan, leukocyte alpha interferon, imiquimod, MDX-010 (anti-CTLA-4), melanoma vaccine, mitumomab, molgramostim, Mylotarg™ (gemtuzumab ozogamicin), Neupogen™ (filgrastim), OncoVAC-CL, Ovarex™ (oregovomab), pemtumomab (Y-muHMFG1), Provenge™ (sipuleucel-T), sargaramostim, sizofiran, teceleukin, Theracys™ (BCG or Bacillus Calmette-Guerin), ubenimex, Virulizin™ (immunotherapeutic, Lorus Pharmaceuticals), Z-100 (Specific Substance of Maruyama or SSM), WF-10 (tetrachlorodecaoxide or TCDO), Proleukin™ (aldesleukin), Zadaxin™ (thymalfasin), Zenapax™ (daclizumab), Zevalin™ (90Y-ibritumomab tiuxetan) and the like.

Biological response modifiers are agents that modify defense mechanisms of living organisms or biological responses, such as survival, growth or differentiation of tissue cells to direct them to have anti-tumor activity, and include krestin, lentinan, sizofiran, picibanil, PF-3512676 (CpG-8954), ubenimex and the like.

Pyrimidine analogs include cytarabine (cytosine arabinoside, ara C or arabinoside C), doxifluridine, Fludara™ (fludarabine), 5-FU (5-fluorouracil), floxuridine, Gemzar™ (gemcitabine), Tomudex™ (raltitrexed), triacetyluridine, Troxatyl™ (troxacitabine) and the like.

Purine analogs include Lanvis™ (thioguanine), Purinethol™ (mercaptopurine) and the like.

Antimitotic agents include batabulin, epothilone D (KOS-862), N-(2-((4-hydroxyphenyl)amino)pyridin-3-yl)-4-methoxybenzenesulfonamide, ixabepilone (BMS-247550), paclitaxel, Taxotere™ (docetaxel), larotaxel (PNU-100940, RPR-109881 or XRP-9881), patupilone, vinflunine, ZK-EPO (synthetic epothilone) and the like.

Ubiquitin ligase inhibitors include MDM2 inhibitors such as nutlins, NEDD8 inhibitors such as MLN4924, and the like.

Compositions of this invention can also be used as radiosensitizers that enhance the efficacy of radiotherapy. Examples of radiotherapy include, but are not limited to, external beam radiotherapy (XBRT), teletherapy, brachytherapy, sealed-source radiotherapy, unsealed-source radiotherapy and the like.

Additionally or alternatively, a composition of the present invention can be administered in combination therapy with one or more antitumor or chemotherapeutic agents selected from Abraxane™ (ABI-007), ABT-100 (farnesyl transferase inhibitor), Advexin™ (Ad5CMV-p53 vaccine or contusugene ladenovec), Altocor™ or Mevacor™ (lovastatin), Ampligen™ (poly(I)-poly(C12U), a synthetic RNA), Aptosyn™ (exisulind), Aredia™ (pamidronic acid), arglabin, L-asparaginase, atamestane (1-methyl-3,17-dione-androsta-1,4-diene), Avage™ (tazarotene), AVE-8062 (combretastatin derivative), BEC2 (mitumomab), cachectin or cachexin (tumor necrosis factor), Canvaxin™ (melanoma vaccine), CeaVac™ (cancer vaccine), Celeuk™ (celmoleukin), histamine including Ceplene™ (histamine dihydrochloride), Cervarix™ (ASO4 adjuvant-adsorbed human papilloma virus (HPV) vaccine), CHOP (Cytoxan™ (cyclophosphamide) +Adriamycin™ (doxorubicin)+Oncovin™ (vincristine)+ prednisone), combretastatin A4P, Cypat™ (cyproterone), DAB(389)EGF (catalytic and translocation domains of diphtheria toxin fused via a His-Ala linker to human epidermal growth factor), dacarbazine, dactinomycin, Dimericine™ (T4N5 liposome lotion), 5,6-dimethylxanthenone-4-acetic acid (DMXAA), discodermolide, DX-8951f (exatecan mesylate), eniluracil (ethynyluracil), squalamine including Evizon™ (squalamine lactate), enzastaurin, EPO-906 (epothilone B), Gardasil™ (quadrivalent human papilloma virus (Types 6, 11, 16, 18) recombinant vaccine), Gastrimmune™, Genasense™ (oblimersen), GMK (ganglioside conjugate vaccine), GVAX™ (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, Junovan™ and Mepact™ (mifamurtide), lonafarnib, 5,10-methylenetetrahydrofolate, miltefosine (hexadecylphosphocholine), Neovastat™ (AE-941), Neutrexin™ (trimetrexate glucuronate), Nipent™ (pentostatin), Onconase™ (ranpirnase, a ribonuclease enzyme), Oncophage™ (vitespen, melanoma vaccine treatment), OncoVAX™ (IL-2 vaccine), Orathecin™ (rubitecan), Osidem™ (antibody-based cell drug), Ovarex™ MAb (murine monoclonal antibody), paclitaxel albumin-stabilized nanoparticle, paclitaxel, Pandimex™ (aglycone saponins from ginseng comprising 20(S)-protopanaxadiol (aPPD) and 20(S)-protopanaxatriol (aPPT)), panitumumab, Panvac™ (investigational cancer vaccine), pegaspargase, peginterferon alfa (PEG interferon A), phenoxodiol, procarbazine, rebimastat, Removab™ (catumaxomab), Revlimid™ (lenalidomide), RSR13 (efaproxiral), Somatuline™ LA (lanreotide), Soriatane™ (acitretin), staurosporine (Streptomyces staurospores), talabostat (PT100), Targretin™ (bexarotene), Taxoprexin™ (docosahexaenoic acid (DHA)+paclitaxel), Telcyta™ (canfosfamide, TLK-286), Temodar™ (temozolomide), tesmilifene, tetrandrine, thalidomide, Theratope™ (STn-KLH vaccine), Thymitaq™ (nolatrexed dihydrochloride), TNFerade™ (adenovector: DNA carrier containing the gene for tumor necrosis factor-α), Tracleer™ or Zavesca™ (bosentan), Trans-MID-107R™ (KSB-311, diphtheria toxins), tretinoin (retin-A), Trisenox™ (arsenic trioxide), Ukrain™ (derivative of alkaloids from the greater celandine plant), Virulizin™, Vitaxin™ (anti-αvβ3antibody), Xcytrin™ (motexafin gadolinium), Xinlay™ (atrasentan), Xyotax™ (paclitaxel poliglumex), Yondelis™ (trabectedin), ZD-6126 (N-acetyl-colchinol-O-phosphate), Zinecard™ (dexrazoxane), zoledronic acid, zorubicin and the like.

In one embodiment, a composition of the invention, for example such a composition comprising N-(4-{4-amino-7-[1-(2-hydroxyethyl)-1H-pyrazol-4-yl]thieno[3,2-c]mpyridin-3-yl}phenyl)-N'-(3-fluorophenyl)urea or a salt thereof, is administered in a therapeutically effective amount to a subject in need thereof to treat cancer.

Examples include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor in a mammal, In a more particular embodiment, a composition of the invention, is administered in a therapeutically effective amount to a subject in need thereof to treat myelodysplastic syndrome, acute myeloid leukemia, colorectal cancer, non-small cell lung cancer, and ovarian cancer.

According to any of these embodiments, the composition is administered in combination therapy with one or more additional therapeutic agents.

As in other embodiments, administration according to the present embodiment can be with or without food, i.e., in a non-fasting or fasting condition. It is generally preferred to administer the present compositions to a non-fasting patient.

EXAMPLES

The following examples are merely illustrative, and do not limit this disclosure in any way. Trademarked ingredients used in the examples, include:
Eudragit® L 100-55: Methacrylic Acid—Ethyl Acrylate Copolymer;
Kollidon® VA64: vinylpyrrolidone-vinyl acetate copolymer;
Kollidon® SR: polyvinyl acetate and povidone matrix;
Tween® 20: polysorbate 20 surfactant;
Cremophor® RH 40: Polyoxyl 40 Hydrogenated Castor Oil
Gelucire® 44/14: polyethylene glycol glycerides Example 1

Preparation of Solid Dispersions

N-(4-{4-amino-7-[1-(2-hydroxyethyl)-1H-pyrazol-4-yl]thieno[3,2-c]pyridin-3-yl}phenyl)-N'-(3-fluorophenyl)urea free base (hereinafter API) was mixed with an optional acid, surfactant(s) and water-soluble polymer(s) in the following weight ratios:
Example 1A: 6% API:3.5% Citric Acid:20% Tween® 20:10% Poloxamer 124:60.5% PEG-1450
Example 1B: 10% API:6% Citric Acid:10% Tween® 20:10% Poloxamer 124:24% HPMC-E5:40% PVP K17
Example 1C: 6% API:3% Citric Acid:20% Tween® 20:71% PEG-1450
Example 1D: 7.5% API:4.5% Citric Acid, 10% Tween® 20:10% Cremophor® RH 40:25% HPMC-E5: 43% PVP K17
Example 1E: 10% API:6% Citric Acid, 10% Tween® 20:10% Cremophor® RH 40:24% HPMC-E5:40% PVP K17
Example 1F: 5% API:3% Citric Acid:20% Tween® 20:27% HPMC-E5:45% PVP K30
Example 1G: 5% API:6% Citric Acid:20% Tween® 20:24% HPMC-E5:40% PVP K30
Example 1H: 5% API:3% Citric Acid:20% Tween® 20:72% HPMC-E5
Example 1I: 5% API:3% Citric Acid:20% Tween® 20:67% PEG-8000
Example 1J: 10% API:3% Citric Acid:10% Tween® 20:10% Poloxamer 124:64% HPMC-E5
Example 1K: 5% API:2% Citric Acid:10% Tween® 20:83% PEG-3350
Example 1L: 10% API:4% Citric Acid:10% Tween® 20:76% HPMC E5
Example 1M: 10% API, 20% Tween® 20:70% HPMC-AS L
Example 1N: 5% API:3% Citric Acid:25% Tween® 20:67% PEG-3350
Example 1O: 5% API:2% Citric Acid:10% Tween® 20:83% PVP K30
Example 1P: 10% API:6% Citric Acid:10% Tween® 20:10% Poloxamer 124:64% PVP K30
Example 1Q: 5% API:3% Citric Acid:20% Tween® 20:72% PVP K30
Example 1R: 10% API:6% Citric Acid:10% Tween® 20:30% HPMC-E5:44% PVP K30
Example 1S: 5% API:4% Citric Acid:91% Gelucire® 44/14
Example 1T: 12.5% API:7.5% Citric Acid:20% Tween® 20:22.5% HPMC-E5:37.5% PVP K30
Example 1U: 15% API:9% Citric Acid:20% Tween® 20:21% HPMC-E5:35% PVP K30
Example 1V: 20% API:12% Citric Acid:20% Tween® 20:18% HPMC-E5:30% PVP K30
Example 1W: 10% API:6% Citric Acid:10% Tween® 20:10% Poloxamer 407:24% HPMC-E5:40% PVP K17
Example 1X: 10% API:6% Citric Acid:10% Tween® 20:10% Poloxamer 188:24% HPMC-E5:40% PVP-K17
Example 1Y: 5% API:2% Citric Acid:10% Tween® 20:83% Eudragit® L 100-55
Example 1Z: 10% API:6% Citric Acid:10% Tween® 20:10% Poloxamer 124:24% HPMC-E5:40% PVP K30
Example 1AA: 10% API:6% Citric Acid:20% Tween® 20:24% HPMC-E3:40% PVP K30
Example 1AB 10T API:20% Tween® 20:70% HPMC-AS M
Example 1AC: 10% API:20% Tween® 20:70% HPMC-AS H Example 1AD: 10% API:6% Citric Acid: 20% Tween® 20:24% HPMC-E3: 40% PVP K17

Example 1AE: 10% API:6% Citric Acid:10% Tween® 20:10% Gelucire® 44/14:24% HPMC-E5:40% PVP K17

Example 1AF: 5% API:4% Citric Acid:91% Vitamin E TPGS

Example 1AG: 10% API:4% Citric Acid:10% Tween® 20:76% Kollidon® VA64

Example 1AH: 10% API:7% Citric Acid:83% Kollidon® SR

Example 1AI: 10% API:6% Citric Acid:20% Tween® 20:24% HPMC-K3:40% HPMC-K3

Example 1AJ: 5% API:2% Citric Acid:10% Tween® 20:83% Kollidon® VA64

Example 1AK: 10% API:6% Citric Acid:20% Tween® 20:24% HPMC-K3:40% PVP K30

The mixture of ingredients in each case were dissolved in aqueous solvent and a water-miscible organic solvent, e.g., acetone or tetrahydrofuran, between ambient temperature at 70° C. The solvent was removed by either rotary evaporation at 65° C. in vacuo or using a spray-dryer operating at 85° C., and the resulting solid dispersion was allowed to cool to ambient temperature.

The solid dispersion in each case was sieved through a 30-mesh screen to provide a powder of reduced particle size. The resulting solid dispersion was dried under vacuum at approximately 100° C.

Example 2

Pharmacokinetics of Solids Dispersion in a Dog Model

Single-dose pharmacokinetics of the solid dispersions were evaluated in fasted beagle dogs (n=3) after a 10, 25, or 50 mg oral dose of solid dispersion in hard gelatin capsule followed by 10 ml water. Approximately 30 min prior to drug administration, each dog received a 100-mg/kg subcutaneous (sc) dose of histamine Food was provided to the animals approximately 4 hours after dosing. Serial heparinized blood samples were obtained from a jugular vein of each animal prior to dosing and 0.25, 0.5, 1, 1.5, 2, 3, 4, 6, 9, 12, 15 and 24 hours after administration. Plasma was separated by centrifugation (2,000 rpm for 10 minutes at approximately 4° C.) and API was isolated using protein precipitation with acetonitrile.

The area under the plasma concentration-time curve from 0 to t hours (time of the last measured plasma concentration) after dosing ($AUC_{0-t}$) was calculated using the linear trapezoidal rule for the plasma concentration-time profiles. The residual area extrapolated to infinity, determined as the final measured plasma concentration ($C_t$) divided by the terminal elimination rate constant ($\beta$), was added to $AUC_{0-t}$ to produce the total area under the curve ($AUC_{0-\infty}$). The bioavailability was calculated as the dose-normalized $AUC_{0-\infty}$ from oral dosing divided by the corresponding value derived from i.v. (intravenous) dosing, administered as a slow bolus to a jugular vein under light ether anesthetic.

PK parameters for the dispersions are presented in Table 1.

TABLE 1

PK parameters of solid dispersion compositions in dog (n = 3)

| Example | Dose mg | T½ h | $C_{max}$ µg/ml | $C_{max}/D$ µg/ml per mg/kg | $T_{max}$ h | AUC µg · h/ml | AUC/D µg · h/ml per mg/kg | F % |
|---|---|---|---|---|---|---|---|---|
| 1A | 10 | 5.2 | 0.50 | 0.46 | 2.0 | 2.8 | 2.6 | 30.8 |
| 1A | 25 | 4.7 | 0.91 | 0.35 | 2.0 | 5.8 | 2.2 | 26.4 |
| 1A | 50 | 5.4 | 2.16 | 0.41 | 2.8 | 14.0 | 2.6 | 31.2 |
| 1B | 10 | 4.8 | 0.46 | 0.54 | 3.0 | 2.5 | 2.9 | 34.4 |
| 1B | 25 | 5.1 | 0.90 | 0.41 | 2.8 | 5.3 | 2.4 | 28.1 |
| 1B | 50 | 4.2 | 1.30 | 0.26 | 2.3 | 7.7 | 1.5 | 18.2 |
| 1C | 10 | 4.7 | 0.37 | 0.43 | 2.8 | 1.9 | 2.2 | 25.9 |
| 1C | 25 | 4.2 | 1.06 | 0.48 | 2.0 | 5.0 | 2.3 | 26.9 |
| 1C | 50 | 4.3 | 1.82 | 0.38 | 2.0 | 8.9 | 1.8 | 21.7 |
| 1D | 10 | 5.0 | 0.32 | 0.33 | 2.3 | 1.87 | 1.93 | 22.9 |
| 1D | 25 | 5.1 | 0.87 | 0.39 | 2.1 | 4.11 | 1.84 | 21.8 |
| 1D | 50 | 4.9 | 1.60 | 0.36 | 2.6 | 7.87 | 1.80 | 21.4 |
| 1E | 10 | 5.1 | 0.38 | 0.36 | 2.7 | 2.4 | 2.3 | 26.1 |
| 1F | 10 | 5.9 | 0.59 | 0.55 | 1.7 | 3.14 | 2.91 | 34.6 |
| 1G | 10 | 5.9 | 0.41 | 0.39 | 2.5 | 2.7 | 2.6 | 29.5 |
| 1H | 10 | 5.4 | 0.36 | 0.36 | 2.5 | 2.2 | 2.2 | 25.9 |
| 1I | 10 | 6.9 | 0.35 | 0.33 | 2.7 | 2.3 | 2.2 | 25.7 |
| 1J | 10 | 5.1 | 0.43 | 0.44 | 2.3 | 2.0 | 2.1 | 24.9 |
| 1K | 10 | 4.3 | 0.28 | 0.28 | 3.3 | 2.1 | 2.1 | 24.4 |
| 1L | 10 | 4.4 | 0.32 | 0.29 | 2.7 | 2.3 | 2.0 | 24.2 |
| 1M | 10 | 6.1 | 0.44 | 0.40 | 3.0 | 2.2 | 1.98 | 23.5 |
| 1N | 10 | 5.2 | 0.33 | 0.30 | 1.8 | 2.2 | 2.0 | 23.2 |
| 1O | 10 | 4.8 | 0.35 | 0.34 | 3.3 | 2.0 | 1.92 | 22.8 |
| 1P | 10 | 5.0 | 0.31 | 0.29 | 3.3 | 2.0 | 1.91 | 22.7 |
| 1Q | 10 | 6.6 | 0.31 | 0.31 | 2.3 | 1.9 | 1.9 | 22.3 |
| 1R | 10 | 4.8 | 0.26 | 0.30 | 2.3 | 1.6 | 1.8 | 21.3 |
| 1S | 10 | 5.7 | 0.32 | 0.28 | 2.3 | 1.9 | 1.7 | 20.2 |
| 1T | 10 | 9.0 | 0.32 | 0.31 | 1.8 | 1.77 | 1.67 | 19.9 |
| 1U | 10 | 6.6 | 0.31 | 0.27 | 3.3 | 1.92 | 1.66 | 19.7 |
| 1V | 10 | 7.2 | 0.36 | 0.34 | 2.2 | 1.68 | 1.58 | 18.8 |
| 1W | 10 | 5.4 | 0.30 | 0.29 | 2.2 | 1.7 | 1.6 | 18.8 |
| 1X | 10 | 5.3 | 0.33 | 0.33 | 3.0 | 1.6 | 1.6 | 18.6 |
| 1Y | 10 | 4.5 | 0.43 | 0.38 | 2.5 | 1.8 | 1.56 | 18.5 |
| 1Z | 10 | 4.8 | 0.27 | 0.26 | 1.3 | 1.5 | 1.47 | 17.5 |
| 1AA | 10 | 4.5 | 0.30 | 0.27 | 3.0 | 1.6 | 1.4 | 17.0 |
| 1AB | 10 | 3.3 | 0.29 | 0.30 | 2.3 | 1.4 | 1.42 | 16.9 |
| 1AC | 10 | 5.6 | 0.21 | 0.20 | 2.5 | 1.4 | 1.32 | 15.7 |

TABLE 1-continued

PK parameters of solid dispersion compositions in dog (n = 3)

| Example | Dose mg | T½ h | $C_{max}$ µg/ml | $C_{max}$/D µg/ml per mg/kg | $T_{max}$ h | AUC µg·h/ml | AUC/D µg·h/ml per mg/kg | F % |
|---|---|---|---|---|---|---|---|---|
| 1AD | 10 | 5.1 | 0.19 | 0.18 | 2.2 | 1.3 | 1.3 | 14.5 |
| 1AE | 10 | 3.8 | 0.24 | 0.24 | 3.7 | 1.2 | 1.2 | 14.3 |
| 1AF | 10 | 7.9 | 0.21 | 0.19 | 1.7 | 1.3 | 1.2 | 14.0 |
| 1AG | 10 | 4.0 | 0.13 | 0.14 | 3.0 | 1.07 | 1.10 | 13.1 |
| 1AH | 10 | 5.4 | 0.15 | 0.15 | 2.3 | 0.9 | 0.88 | 10.4 |
| 1AI | 10 | 4.0 | 0.15 | 0.15 | 3.3 | 0.9 | 0.9 | 10.2 |
| 1AJ | 10 | 4.5 | 0.11 | 0.11 | 2.5 | 0.6 | 0.61 | 7.3 |
| 1AK | 10 | 1.3 | 0.12 | 0.13 | 2.2 | 0.4 | 0.5 | 5.7 |

Example 3

Pharmacokinetics of Solids Dispersion in a Dog Model

Solid dispersion formulations of the invention were used in an open-label Phase I human study evaluating the safety and pharmacokinetics of N-(4-{4-amino-7[1-(2-hydroxyethyl)-1H-pyrazol-4-yl]thieno[3,2-c]pyridin-3-yl}phenyl)-N'-(3-fluorophenyl)urea as monotherapy in subjects with advanced solid tumors or advanced hematologic malignancies.

The number of subjects that entered the studies and completed at least a portion of the studies are noted. Subjects entered the study and were assigned to receive one of the following doses: 10 mg, 20 mg, 40 mg, 80 mg, 120 mg, 160 mg, and 180 mg. The tablet formulation consisted of solid dispersion powder corresponding to Example 1E with excipients (50% Example 1E: 38.75% microcrystalline cellulose: 10% crospovidone: 1% colloidal silicon dioxide: 0.5% magnesium state).

Doses were administered on Day 1, Day 8, and Day 15 of each 28 day cycle. On Day 1 and Day 15, plasma samples are collected at time 0, 0.5, 1, 2, 3, 4, 6, 8, 10, and 24 hours or 0, 0.5, 1, 2, 3, 4, 6, 8, 10 or 12, 24, 48 and 72 hours after dosing. The plasma concentrations of N-(4- {4-amino-7- [1-(2-hydroxyethyl)-1H-pyrazol-4-yl]thieno[3,2-c]pyridin-3-yl}phenyl)-N'-(3-fluorophenyl)urea were determined, and the values for the pharmacokinetic parameters were calculated and shown in Table 2.

TABLE 2

PK parameters of solid dispersion compositions in humans

| Pharmacokinetic Parameters | 10 mg | | 20 mg | | 40 mg | | 80 mg | |
|---|---|---|---|---|---|---|---|---|
| | Day 1 (N = 6) | Day 15 (N = 6) | Day 1 (N = 3) | Day 15 (N = 3) | Day 1 (N = 2) | Day 15 (N = 2) | Day 1 (N = 5) | Day 15 (N = 5) |
| Terminal Half-Life (h)* | 15.0 ± 3.0 | 12.6 ± 4.4 | 15.5 ± 9.9 | 19.2 ± 6.0 | 9.8, NA | 15.8, 11.5 | 15.3 ± 1.9 | 13.3 ± 4.2 |
| $T_{max}$ (h) | 3.3 ± 0.5 | 3.3 ± 0.8 | 4.0 ± 2.0 | 4.3 ± 1.5 | 3.0, 8.0 | 2.0, 3.0 | 3.0 ± 0.0 | 3.4 ± 1.7 |
| $C_{max}$ (ng/mL)** | 40.6 ± 25.3 | 26.9 ± 15.4 | 62.7 ± 78.3 | 58.4 ± 82.2 | 198, 43.7 | 247, 160 | 160 ± 70.6 | 98.4 ± 36.5 |
| $AUC_\infty$ (µg·h/mL)** | 0.62 ± 0.47 | 0.39 ± 0.17 | 1.11 ± 0.53 | 1.25 ± 1.30 | 1.83, NA | 2.27, 1.64 | 1.85 ± 0.89 | 1.62 ± 0.82 |
| $AUC_{0-24}$ (µg·h/mL)** | 0.40 ± 0.29[a] | 0.27 ± 0.12[a] | 0.34 ± 0.84[b] | 0.47 ± 0.29[b] | 1.51, 0.64 | 1.53, 1.15 | 1.05 ± 0.37[c] | 1.04 ± 0.49[c] |

| | 120 mg | | 160 mg | | 180 mg |
|---|---|---|---|---|---|
| | Day 1 (N = 7) | Day 15 (N = 4) | Day 1 (N = 3) | Day 15 (N = 3) | Day 1 (N = 3) |
| Terminal Half-Life (h)* | 9.7 ± 6.8[a] | 20.4 ± 10.6[d] | 14.3 ± 4.8 | 15.6 ± 3.3 | 9.2 ± 2.3 |
| Tmax (h) | 3.7 ± 2.1 | 4.3 ± 2.5 | 3.3 ± 1.2 | 2.3 ± 1.2 | 4.0 ± 2.02 |
| Cmax (ng/mL)** | 395 ± 272 | 208 ± 84.6 | 265 ± 198 | 178 ± 36.0 | 439 ± 354 |
| AUC∞ (µg·h/mL)** | 4.93 ± 1.65[a] | 4.17 ± 2.41[d] | 3.0 ± 1.84 | 2.59 ± 0.77 | 6.61 ± 2.99 |
| $AUC_{0-24}$ (µg·h/mL)** | 2.47 ± 0.20[d] | 1.84 ± 0.35[b] | 2.36 ± 1.34 | 1.75 ± 0.27 | 5.28 ± 2.35[d] |

*Harmonic Mean and Pseudo Standard Deviation
**Geometric mean ± Pseudo Standard Deviation
[a]N = 5
[b]N = 2
[c]N = 4
[d]N = 3
[e]N = 6

What is claimed is:

1. A solid dispersion product comprising N-(4-{4-amino-7-[1-(2-hydroxyethyl)-1H-pyrazol-4-yl]thieno [3,2-c]pyridin-3-yl}phenyl)-N'-(3-fluorophenyl)urea or a pharmaceutically acceptable salt thereof, at least one pharmaceutically acceptable water-soluble polymeric carrier, and at least one pharmaceutically acceptable surfactant, wherein the N-(4-{4-amino-7-[1-(2-hydroxyethyl)-1H-pyrazol-4-yl]thieno[3,2-c]pyridin-3-yl}phenyl)-N'-(3-fluorophenyl)urea is present in about 1% to about 40% by free base equivalent weight.

2. The solid dispersion product of claim 1, wherein solid dispersion product is amorphous.

3. The solid dispersion product of claim 1, comprising at least one acid.

4. The solid dispersion product of claim 3, wherein the at least one acid comprises from about 0.1 to about 10 equivalents with respect to N-(4-{4-amino-7-[1-(2-hydroxyethyl)-1H-pyrazol-4-yl]thieno [3,2-c]pyridin-3-yl}phenyl)-N'-(3-fluorophenyl)urea.

5. The solid dispersion product of claim 3, wherein the at least one acid is selected from the group consisting of acetic acid, ascorbic acid, benzenesulfonic acid, citric acid, ethanedisulfonic acid, 1-hydroxy-2-napthoic acid, hydrochloric acid, hydrobromic acid, lactic acid, maleic acid, malic acid, malonic acid, methanesulfonic acid, phosphoric acid, sulfuric acid, succinic acid, tartaric acid, and toluenesulfonic acid.

6. The solid dispersion product of claim 3, wherein the at least one acid is selected from the group consisting of citric acid, maleic acid, malic acid, malonic acid, succinic acid, and tartaric acid.

7. The solid dispersion product of claim 3, wherein the at least one acid is citric acid.

8. The solid dispersion product of claim 1, wherein the N-(4-{4-amino-7-[1-(2-hydroxyethyl)-1H-pyrazol-4-yl]thieno[3,2-c]pyridin-3-yl}phenyl)-N'-(3-fluorophenyl)urea is present in about 5% to about 15% by free base equivalent weight.

9. The solid dispersion product of claim 1, wherein the N-(4-{4-amino-7-[1-(2-hydroxyethyl)-1H-pyrazol-4-yl]thieno[3,2-c]pyridin-3-yl}phenyl)-N'-(3-fluorophenyl)urea is present in about 8% to about 12% by free base equivalent weight.

10. The solid dispersion product of claim 1, wherein the at least one polymeric carrier is present in an amount of about 40% to about 85% by weight and the at least one surfactant is present in an amount of about 5% to about 30% by weight.

11. The solid dispersion product of claim 1, wherein at least one polymeric carrier is selected from the group consisting of homopolymers and copolymers of N-vinyl lactams, cellulose esters, cellulose ethers, high molecular weight polyalkylene oxides, polyacrylates, polymethacrylates, polyacrylamides, vinyl acetate polymers, oligo- and polysaccharides, and mixtures thereof.

12. The solid dispersion product of claim 1, wherein the at least one polymeric carrier is selected from the group consisting of polyvinylpyrrolidone, hydroxypropyl methylcellulose, and mixtures thereof.

13. The solid dispersion product of claim 1, wherein the at least one surfactant is selected from the group consisting of polyethylene glycol glyceride derivatives, polyoxyethylene castor oil derivatives, fatty acid monoesters of sorbitan, polysorbates, poloxamers, α-tocopheryl polyethylene, glycol succinate, and mixtures thereof.

14. The solid dispersion product of claim 1, wherein the at least one surfactant is selected from the group consisting of polysorbates, polyoxyethylene castor oil derivatives, and mixtures thereof.

15. An orally deliverable pharmaceutical dosage form comprising the solid dispersion product of claim 1.

16. The dosage form of claim 15, containing at least one additive selected from the disintegrants, lubricants, and bulking agents.

* * * * *

UNITED STATES PATENT AND TRADEMARK OFFICE
CERTIFICATE OF CORRECTION

| | | |
|---|---|---|
| PATENT NO. | : 8,557,995 B2 | Page 1 of 1 |
| APPLICATION NO. | : 13/154562 | |
| DATED | : October 15, 2013 | |
| INVENTOR(S) | : Miller et al. | |

It is certified that error appears in the above-identified patent and that said Letters Patent is hereby corrected as shown below:

In the Specification

Column 13, line 65, detailed description: "NCB-018424" to read as --INCB-018424--

Column 16, line 64, detailed description: "mpyridin" to read as --pyridin--

Signed and Sealed this
Eighth Day of July, 2014

Michelle K. Lee
*Deputy Director of the United States Patent and Trademark Office*